United States Patent [19]

Mehansho et al.

[11] Patent Number: 4,992,282

[45] Date of Patent: *Feb. 12, 1991

[54] STABLE NUTRITIONAL VITAMIN AND MINERAL SUPPLEMENTED BEVERAGE

[75] Inventors: Haile Mehansho, Fairfield; Donald L. Hughes, Cincinnati, both of Ohio; Gunther M. Nakel, Aurora, Ind.; David C. Heckert, Oxford, Ohio

[73] Assignee: The Procter & Gamble Company, Cincinnati, Ohio

[*] Notice: The portion of the term of this patent subsequent to Nov. 22, 2005 has been disclaimed.

[21] Appl. No.: 348,745

[22] Filed: May 8, 1989

[51] Int. Cl.$^5$ .............................................. A23L 2/02
[52] U.S. Cl. ...................................... 426/72; 426/73; 426/74; 426/599
[58] Field of Search ................... 426/74, 590, 599, 72, 426/73; 514/502

[56] References Cited

U.S. PATENT DOCUMENTS

| | | | |
|---|---|---|---|
| 3,114,641 | 12/1963 | Sperti | 426/599 |
| 3,652,290 | 3/1972 | Hammes et al. | 99/28 |
| 3,734,742 | 5/1973 | Morse | 99/28 |
| 3,809,773 | 5/1974 | Bookwalter | 426/380 |
| 3,958,017 | 5/1976 | Morse | 426/72 |
| 4,214,996 | 7/1980 | Buddemeyer et al. | 252/1 |
| 4,351,735 | 9/1982 | Buddemeyer et al. | 252/1 |
| 4,486,413 | 12/1986 | Wisenberger | 424/177 |
| 4,582,709 | 4/1986 | Peters et al. | 426/74 |
| 4,722,847 | 2/1988 | Heckert | 426/74 |
| 4,737,367 | 4/1988 | Langer | 426/599 |
| 4,786,510 | 11/1988 | Nakel et al. | 426/74 |
| 4,786,518 | 11/1988 | Nakel | 426/531 |

FOREIGN PATENT DOCUMENTS

| | | |
|---|---|---|
| 0075114 | 8/1982 | European Pat. Off. . |
| 0246177 | 5/1987 | European Pat. Off. . |
| 2219778 | 4/1976 | France . |
| 5697248 | 7/1979 | Japan . |

OTHER PUBLICATIONS

The Effect of Chemical Agents, Beverages and Spinach on the In Vitro Solubilization of Iron from Cooked Pinto Beans; Nakao Kojima, Diane Wallace, George Bates; The Journal of Clinical Nutrition 34: Jul. 1981, pp. 1392-1401.
Effect of Product Formulation, Process and Meal Composition of In Vitro Estimated Iron Availability from Cereal Containing Breakfast Meals, B. L. Carlson, D. D. Miller, vol. 48 (1983), Journal of Food Science.
Absorption of Iron from Breakfast Meals—L. Rossander, L. Hallberg, E. Bjorn-Rasmussen—The American Journal of Clinical Nutrition 32: Dec. 1979, pp. 2484-2489.
Latent Iron Deficiency and Effect of Prophylactic Administration of Medicamentous Iron on the Red Blood Composition of Healthy Young Children—E. G. Metrevily; Pediatriyc (Moscow) 1977, 12, pp. 17-19.
Nutrients and Nutrition of Citrus Fruits, S. V. Ting, from "Citrus Nutrition and Quality", Steve Nagy and John Attaway ACS, 1980.
Measurements of Iron Absorption from Prenatal Multivitamin-Mineral Supplements; P. A. Seligman, et al.; Obstetrics & Gynecology, pp. 356-362, Aug. 1983.
Calcium Inhibition of Inorganic Iron Absorption in Rats; Barton, Conrad and Parmley—Gastroenterology, 1983-84, pp. 90-101.
The Effects of Organic Acids, Phytates and Polyphenols on the Absorption of Iron from Vegetables; Gillooly, et al; Br. Journal of Nutrition (1983) 49, 331-343.
Goodman & Gilman, "The Pharmacological Basis of Therapeutics", 5th Edition, pp. 1315-1316 (1975).
Remington's Pharmaceutical Sciences, 15th Edition, p. 393 (1975).
Low Bioavailability of Carbonyl Iron in Man: Studies on Iron Fortification of Wheat Flour—Hallberg, et al.—The Am. Journal of Clinical Nutrition 43, Jan. 1986, pp. 59-67.
Interaction of Vitamin C and Iron; Lynch & Cook, New York Academy of Sciences (1980).
Food Acidulants, Wm. H. Gardner; Allied Chemical Corp. (1966).
Improvement of Iron Nutrition in Developing Countries: Comparison of Adding Meat, Soy Protein, Ascorbic Acid, Citric Acid, and Ferrous Sulphate on Iron Absorption from a Simple Latent American-Type of Meal; Hallberg & Rossander—The Am. Journal of Clinical Nutrition 39: Apr. 1984, pp. 577-583.
Effects of Calcium and Phosphorus Salts on the Utilization of Iron by Anemic Rats—Chapman and Campbell.

*Primary Examiner*—Carolyn Paden
*Attorney, Agent, or Firm*—Rose Ann Dabek; Jerry J. Yetter; Richard C. Witte

[57] ABSTRACT

Vitamin and mineral-fortified beverages, especially carbonated beverages are disclosed. These beverages are stable and contain vitamin A in the form of encapsulated β-carotene, vitamin C and riboflavin. The beverages show enhanced calcium and iron absorption.

20 Claims, No Drawings

STABLE NUTRITIONAL VITAMIN AND MINERAL SUPPLEMENTED BEVERAGE

TECHNICAL FIELD

The present invention relates to improvements in nutritious vitamin and mineral supplemented beverages which contain vitamin C (ascorbic acid), encapsulated β-carotene (vitamin A) and riboflavin, iron and calcium compounds. The supplement can contain other minerals, such as zinc and copper, and other B vitamins. In particular, methods for preparing stable nutritious beverages having enhanced mineral bioavailability are provided.

BACKGROUND OF THE INVENTION

Vitamin and mineral supplements for human and veterinary use are commonplace. Recently, it has become recognized that certain groups of the human population may require quite high intakes of minerals, such as calcium, to prevent or alleviate certain disease states, for example, osteoporotic conditions. The medical management of certain anemias can be handled rather well by increasing the daily intake of iron. Some diets, or heavy physical exercise, may require the intake of considerable quantities of minerals apart from those generally obtained through what otherwise would be considered a balanced diet.

Vitamin supplementation is also important, primarily for those who have inadequate diets, including growing children. In Central and South American countries where the dietary intake of minerals and vitamins are low in the general population, such a nutritional supplement would have great value.

Commercially available mineral supplements, are useful in many circumstances where enhanced mineral uptake is desirable. However, adhering to a regimen which requires separate intake of vitamin and mineral supplements can give suboptimal results, simply because the regimen requires a change in the normal habits and practices of the user. It would be more convenient if the vitamins and minerals could be administered conjointly in a convenient form which would not require extra attention, planning and implementation by the user.

In addition, some materials interfere with the absorption of iron and calcium. The administration of calcium, iron and vitamins in a format which enhances absorption of the calcium and iron is highly desirable.

There are well-recognized problems associated with adding both vitamins and mineral supplements to foods and beverages. For example, many calcium supplements tend to be rather insoluble, and, therefore, not very useful in beverages, or tend to have a "chalky" taste or mouth feel. Iron supplements tend to discolor foodstuffs, or to be organoleptically unsuitable. Moreover, it is particularly difficult to formulate foods and, especially, beverages, containing mixtures of iron supplements and calcium supplements, inasmuch as these minerals tend to interact. This interaction not only affects the organoleptic and aesthetic properties of the foods and beverages, but also undesirably affects the nutritional bioavailability of these minerals, themselves.

Vitamins tend to decompose over time in beverages. It is well known that orange juice and other citrus beverages lose their vitamin C content over time. Vitamin C (ascorbic acid) acts as an anti-oxidant and therefore is itself reduced or changed when added to beverages. Vitamin A and its precursor, β-carotene, and riboflavin are also subject to degradation over time.

It would be desirable, therefore, to have vitamin C, vitamin A or β-carotene and riboflavin present with iron and calcium supplements wherein bioavailability of both minerals and of the vitamins is optimized. It would also be useful to have such supplements which can be used in food and beverage compositions without undesirably affecting organoleptic or aesthetic properties.

It is an object of the present invention to provide mixed vitamin and iron-calcium mineral supplements which fulfill these unmet needs.

It is a further object of this invention to provide beverages and beverage concentrates which are supplemented with vitamin C, β-carotene, riboflavin, iron and calcium and which are stable on storage.

It is a further object herein to provide means for enhancing biological uptake of iron and calcium minerals, especially from fruit flavored beverages, including citrus beverages in compositions which are both palatable and stable by the addition of these vitamins.

These and other objects are secured herein, as will be seen from the following disclosure.

BACKGROUND ART

The depression of iron absorption by high levels of calcium was recognized as early as 1940. Since then, various groups have repeatedly confirmed the significant inhibition of iron absorption by calcium. In postmenopausal women, calcium supplements, namely, calcium carbonate and calcium hydroxyapatite, markedly reduced iron absorption. In addition, calcium carbonate in prenatal multivitamin mineral supplements was identified as an inhibitor of absorption in nonpregnant women. Thus, individuals that consume high calcium and marginal amounts of iron simultaneously could develop iron deficiency anemia. See: Kletzein, S.W., "Iron Metabolism", *J. Nutr.* 19, 187-97 (1940); Chapman, D.G. and Campbell, J.A., "Effect of Calcium and Phosphorus Salts in the Utilization of Iron by Anemic Rats", *Br. J. Nutr.*, 11, 127-133 (1957); Barton, J.C., Conrad, M.E. and Parmley, R.T., "Calcium Inhibition of Inorganic Iron Absorption in Rats", *Gastroenterology*, 84, 90-101 (1983); and Seligman, E.R. and Allen, R.M., "Measurement of Iron Absorption from Prenatal Multivitamin Supplements", *Obstetrics and Gyn.*, 61, 356-362. (1983)

The calcium and iron mineral supplements useful in this invention are disclosed in U.S. Pat. No. 4,786,510 issued to Nakel, et al (1988) which describes mineral supplements containing calcium-citrate-malate materials and iron sugar complexes. The iron mineral supplements are described in U.S. Pat. No. 4,786,518 issued to Nakel et al (1988). The calcium-citrate-malate materials are described in U.S. Pat. No. 4,722,847 issued to Heckert (1988). Increased iron absorption from these iron and calcium mineral supplements by the addition of sorbitol has also been shown.

Ascorbic acid is a material which enhances the absorption of iron from foods. In particular, orange juice has been recognized as an enhancer to iron absorption for a long time. Orange juice consumed with a typical western type breakfast reportedly increased iron bioavailability by 2.5-fold. In an in vitro system, addition of orange juice to breakfast meals and cooked pinto beans reportedly caused a dramatic increase in iron solubility. According to Rossander, et al, the reduction of iron absorption by tea was alleviated by orange juice. See: Lynch, S.R. Cook, J.D., "Interaction of Vitamin C and Iron", *Annals New York Academy of Sciences*, 32–44 (1980); Rossander, L., Hallberg, L. and Bjorn-Rasmussen, E., "Absorption of Iron from Breakfast Meals," *Am. J. Clin. Nutr.*, 32, 2484–2489 (1979); Carlson, B.L. and Miller, D.D., "Effects of Product Formulation, Processing and Meal Composition on In Vitro Estimated Availability from Cereal Containing Breakfast Meals", *J. Food Sci.*, 48, 1211–1216 (1983); and Kojima, N., Wallace, D. and Bates, W.G., "The Effects of Chemical Agents, Beverages and Spinach on the In Vitro Solubilization of Iron from Cooked Pinto Beans", *Am. J. Clin. Nutr.*, 34, 1392–1401 (1981).

See, also, the nutritional literature: Ting, S.V., "Nutrients and Nutrition of Citrus Fruits" in *Citrus Nutrition and Quality* (edit. Nagy, S. and Attaway, J.) 3–24 (Amer. Chem. Soc., 1980); Gillooly, M., Bothwell, T.M., Torrance, J.D., MacPhail, A.P., Derman, D.P., Bezwoda, W.R., Mills, W. and Charlton, R.W., "The Effects of Organic Acids, Phytates and Polyphenols on the Absorption of Iron from Vegetables", *Br. J. Nutr.*, 49, 331–342 (1983); Hallberg, L. and Rossander, L., "Improvement in Iron Nutrition in Developing Countries: Comparison of Adding Meat, Soy Protein, Ascorbic Acid, Citric Acid and Ferrous Sulfate on Iron Absorption for a Simple Latin American Type of Meal", *Am. J. Clin. Nutr.*, 39, 577–583 (1984).

In addition to the foregoing, various mineral supplements, including iron supplements and calcium supplements, are described in the following references.

Certain forms of calcium-citrate-malate are disclosed for use as mineral supplements, including beverages; see Japanese Application Sho 54-173172, date of application Dec. 28, 1979, laid-open Sho 56-97248, Aug. 5, 1981; and see also French Patent No. 2,219,778 (Application No. 73.08643).

Some form of iron sucrate has been administered to children and the effect on hemoglobin reported; see the Russian reference Metrevely, E.G., *PEDIATRIYC* (Moscow) 12, 17–19 1977); *Chem. Abs.* 89:637.

U.S. Pat. No. 4,582,709, to Peters and Derick, Apr. 15, 1986, relates to chewable mineral supplements, and lists, inter alia, various calcium and iron compounds. Vitamin D is listed as an absorption enhancer.

U.S. Pat. No. 4,351,735, to Buddemeyer, et al, Sept. 28, 1982, relates to mineral supplements which contain certain phosphate moieties. Dispersibility of the compositions is said to be enhanced by "hydroxyl sources", e.g., sugars. A synthetic milk containing vitamins is described. (See also U.S. Pat. No. 4,214,996, to Buddemeyer, et al, July 29, 1980, relates generally to the same subject matter as the '735 patent).

The beneficial effect of orange juice on the uptake of iron from dietary sources is described by Carlson and Miller in JOURNAL OF FOOD SCIENCE, 48, 1211 (1983).

U.S. Pat. No. 3,114,641, to Sperti et al, issued Dec. 17, 1963, discloses extended orange juice products obtained by diluting single-strength orange juice or concentrated orange juice. To maintain the flavor of the diluted orange juice product, materials such as calcium chloride, magnesium chloride, sodium or potassium citrates, tartaric and malic acids (or their salts) are included. Ascorbic acid is also added to these compositions.

European Patent Application No. 75,114, published Mar. 30, 1983, discloses protein-containing fruit juice drinks enriched with vitamins and minerals. These drinks contain 30–90% fruit juice (a mixture of 207–70% apple juice, 4–40% white grape juice, 1–10% passion fruit juice and 5–25% lemon juice), 2 to 20% whey protein concentrate, and a mineral salt mixture of potassium, sodium, magnesium, calcium and phosphate. Calcium is present in these drinks at 0.01% to 0.3%, preferably at 0.02% to 0.03%.

European patent application No. 246,177 published Nov. 19, 1987, relates to beverages containing nutritional supplementation with calcium, magnesium, potassium, a sweetener and a stabilizer. The calcium compound is selected from the group of calcium aspartate, calcium orotate and mixtures thereof. Benzoic acid is used to lower the pH of the solution. This material is said to rapidly supply calcium to the body without causing gastric upset and stomach bloating, it is also said to lower blood pressure and accelerate the reduction of blood alcohol in the body.

U.S. Pat. No. 3,734,742 issued to Morse, et al (May 22, 1973) relates to a canned or bottled aqueous beverage containing at least 80% water, a pH of 2 to 3.4, ascorbic acid and ferrous ion. The sources of the ferrous ion are ferrous sulfate, ferrous fumarate, ferrous citrate and ferrous lactate.

U.S. Pat. No. 3,652,290 issued to Hansen, et al (Mar. 28, 1972) relates to vitamin C stabilization by the addition of histidine, glycine, or methionine. Iron salts can be added to the beverage product.

U.S. Pat. No. 3,958,017 issued to Morse, et al (May, 1976) is related to the above patents. This patent relates to vitamin C and natural fruit and vegetable flavored drinks stabilized by the addition of controlled quantities of cysteine without an adverse effect on taste. Metabolically available iron is also stabilized by the cysteine.

SUMMARY OF THE INVENTION

The vitamin and mineral supplements herein most preferably employ iron compounds, e.g. ferrous gluconate and ferrous ascorbate, and also iron-sugar complexes as the iron source. The iron-sugar complexes of the type described more fully hereinafter contain counterions selected from malate, citrate, tartrate, ascorbate, or mixtures thereof. The most preferred iron sources are those in which the iron is in the ferrous (+II) state, although ferric (+III) iron is also acceptable.

In such compositions, the calcium supplement is preferably calcium citrate-malate, and the iron-source is preferably selected from ferrous gluconate/ascorbate, iron sucrate-malate, iron fructate-malate, iron sucrate-citrate, iron fructate-citrate, iron sucrate-ascorbate, iron fructate-ascorbate, or mixtures thereof. (The iron is preferably in the ferrous state.)

The vitamin supplement is an encapsulated $\beta$-carotene, or a stable vitamin A, ascorbic acid (vitamin C) and riboflavin.

Typical beverage or beverage concentrate compositions according to this invention comprise:
(a) at least about 0.05% by weight of fruit or cola flavor, or at least 3% by weight of fruit juice;
(b) a nutritionally supplemental amount of a calcium source, preferably, calcium- citrate-malate;
(c) a nutritionally supplemental amount of iron sugar complex or ferrous gluconate/ascorbate; and
(d) a nutritionally supplemental amount of vitamin C, vitamin A or encapsulated $\beta$-carotene and riboflavin.
(e) water and optionally, a sweetener.

By way of example, the fruit juices and fruit flavors used herein include grape, pear, passion fruit, pineapple, banana or banana puree, apricot, orange, lemon, grapefruit, apple, cranberry, tomato, mango, papaya and mixtures thereof.

Either artificial flavors, e.g. cola, or natural flavors derived from these juices can be used in the beverages. Chocolate flavors and other non-fruit flavors can also be used to make beverages containing the vitamin and mineral supplement.

The invention encompasses beverages, especially juice and cola beverages, which are carbonated in the manner of soft drinks, as well as "still" beverages. The invention also encompasses nectars and full-strength beverages or beverage concentrates which contain at least about 45% by weight of juice.

All ratios, proportions and percentages herein are by weight, unless otherwise specified.

DETAILED DESCRIPTION OF THE INVENTION

The present invention relates to stable vitamin and mineral supplemented beverages. These beverages can be carbonated beverages e.g., flavored seltzer waters, soft drinks or mineral drinks, as well as non-carbonated fruit juices, fruit punches and concentrated forms of these beverages.

As used herein, the term "fruit juice product" refers to both fruit juice beverages and fruit juice concentrates which comprise at least about 45% fruit juice.

As used herein, the term "fruit juice beverage" refers to a fruit juice product which is in a single-strength, ready-to-serve, drinkable form. Fruit juice beverages of the present invention can be of the "full-strength" type which typically comprise at least about 95% fruit juice.

Fruit juice beverages within the scope of the present invention also include extended juice products which are referred to as "nectars". These extended juice products typically comprise from about 50% to about 90% fruit juice. Preferred extended juice products comprise from about 50% to about 70% fruit juice. Nectars usually have added sugars or artificial sweeteners or carbohydrate substitutes.

As used herein, the term "fruit juice concentrate" refers to a fruit juice product which, when diluted with the appropriate amount of water, forms drinkable fruit juice beverages. Fruit juice concentrates within the scope of the present invention are typically formulated to provide drinkable beverages when diluted with 3 to 5 parts by weight water.

As used herein the term "beverage concentrate" or "beverage syrup" refers to a mixture of flavors, water and from about 10% to about 60% sugar or carbohydrate substitute, i.e. sucrose, dextrose, corn syrup solids, fructose, dextrins, polydextrose and mixtures thereof.

As used herein, the term "fruit juice materials" refers to concentrated fruit juice, plus other fruit juice materials such as fruit juice aroma and flavor volatiles, peel oils, and pulp or pomace.

As used herein, the term "citrus juice" refers to fruit juices selected from orange juice, lemon juice, lime juice, grapefruit juice, tangerine juice and mixtures thereof.

As used herein, the term "comprising" means various components can be conjointly employed in the fruit juice beverages and juice concentrates of the present invention. Accordingly, the terms "comprising essentially of" and "consisting of" are embodied in the term comprising.

MINERAL AND VITAMIN COMPONENT

The present invention involves the use of vitamin C in sugar containing beverages to enhance the body's uptake of nutritionally supplemental amounts of iron compounds, or mixtures of iron and calcium compounds, in humans and lower animals. These beverages also contain stable compositions of vitamin A in the form of $\beta$-carotene, vitamin C and riboflavin.

By "nutritional" or "nutritionally-supplemental amount" herein is meant that the vitamin and mineral sources used in the practice of this invention provide a nourishing amount of said minerals and vitamins. This supplemental amount will comprise at least 10% of the Recommended Daily Allowance (RDA) of the daily intake of said mineral, and for vitamins, this supplemental amount will be at least 25% and preferably at least 50% of the Recommended Daily Allowance (RDA). The RDA for vitamins and minerals is as defined in The United States of America (see Recommended Daily Dietary Allowance-Food and Nutrition Board, National Academy of Sciences-National Research Council). More generally, mineral supplements will contain at least 10%, more typically 50% to 300%, of the RDA per unit dose of the supplement. In beverage products of the type disclosed herein, the nutritionally supplemental amount will generally comprise more than 3% of the RDA for minerals and preferably 10%-100% RDA, most preferably 10%-30% of the RDA, per unit portion of the food or beverage product. For vitamins, the nutritionally supplemental amount will comprise more than 10%, preferably about 20% to about 100% and, most preferably, from about 50% to about 150% RDA. Of course, it is recognized that the preferred daily intake of any mineral or vitamin may vary with the user. For example, pregnant, lactating, or postmenopausal females and children under 17 may require an increased intake of calcium, over the usual RDA. Persons suffering with anemia may require an increased intake of iron. Persons suffering vitamin deficiencies or who have poor diets will require more vitamins A, C and riboflavin, particularly growing children in South and Central America. Such matters are familiar to physicians and nutritional experts, and usage of the compositions of the present invention may be adjusted accordingly.

In general, the RDA for vitamin C is 60 mg. The RDA for vitamin A is 1 mg. and for $\beta$-carotene the RDA is 6 mg. The RDA of riboflavin is 1.7 mg.

In general, the RDA (iron) ranges from 10 mg per 6 Kg to 18 mg per 54–58 Kg female, depending somewhat on age. Typically, foods and beverages are supplemented with from about 10–25% RDA iron (based per serving) to account for iron which is available from other dietary sources (assuming a reasonably balanced diet). In general, the RDA (calcium) will range from 360 mg per 6 Kg for infants to 1200 mg/54–58 Kg female, depending somewhat on age. Moreover, it can be difficult to supplement beverages with more than 20–30% RDA of calcium (based per serving) without encountering precipitation and/or organoleptic problems. However, this level of supplementation is equivalent to cow's milk in calcium value, and is therefore acceptable. Of course, if iron toxicity and organoleptic quality are not deemed important considerations in individual circumstances, more of the supplements herein can be used.

Encapsulated β-carotene is the vitamin A supplement of choice since it is a precursor or provitamin A and therefore there is no risk of overdoses of this material as with vitamin A. When Vitamin A is consumed in excessive amounts, it can accumulate in the body's fatty tissue. The same problem does not occur with β-carotene.

The vitamin A supplements preferred for use herein are those which exhibit stability in beverage systems. The vitamin A source is preferably an encapsulated or stabilized β-carotene powder which is stable under the pH conditions in the beverage, usually a pH of 2 to about 7. One encapsulation material which provides this stability is dextrin. Similar encapsulation materials can also be used (Roche Vitamins and Fine Chemicals, Nutley, N.J. is a source of encapsulated β-carotene (1% powder)). Dextrin and gum acacia encapsulated β-carotene is stable in beverages for over two months when the beverages are processed and packaged as described hereinafter, yet the β-carotene is bioavailable.

A level of from about 0.0005% or about 0.75 mg/372 gm beverage provides at least 25% of the RDA of vitamin A or β-carotene. Preferably from about 0.00025% to about 0.003% (25% to about 300% RDA) and, most preferably, from about 0.00050% to about 0.0015% β-carotene (75% to 150% RDA) is used in the vitamin and mineral supplements herein.

Any commercially available source of vitamin C can be used herein. Preferably from about 25% to about 300% of the RDA is used in the beverages (0.15g/372g beverage or 0.008% to about 0.09 g/372 g beverage or 0.024%). Most preferably, the amount of vitamin C used is from about 25% to about 150% of the RDA.

Any commercially available source of riboflavin can be used. Preferably from about 20% to about 200% in the beverage (0.34 mg/372 g to 6.8 mg/372 g).

Other vitamins which can be added to the beverage include vitamin $B_6$, niacin, and vitamin $B_{12}$. Other vitamins can also be used.

Other minerals which can be added include zinc and copper. Any soluble salt of these minerals can be used, for example, zinc chloride, zinc sulfate and copper sulfate. A nutritionally supplemental amount of these minerals is used. However, the particular salt used and the level will depend upon their interaction with the iron-sugar and calcium sugar complexes.

The "iron-sugar" complexes preferred for use in the practice of this invention are prepared in the manner described in U.S. Pat. No. 4,786,510 issued to Nakel et al (1988) and U.S. Pat. No. 4,786,518 issued to Nakel et al (1988). Their preparation is described briefly below. (These materials are referred to herein as "complexes", but they may, in fact, exist in solution as complicated, highly-hydrated, protected colloids. However, the term "complex" is used herein for simplicity.) While the iron in these complexes can be in the ferric (iron III) state, it is more preferably in the ferrous (iron II) state. Ferrous iron is better tolerated and utilized by the body than ferric iron. Importantly, ferric iron and common ferrous salts can cause off-flavors in some beverages, after storage; ferric iron can also oxidize and thus degrade the ascorbic acid (Vitamin C) in the beverages. The preferred complexes used herein can conveniently be thought of as iron-sugar-carboxylate complexes, wherein the carboxylate provides the counterion for the ferrous (preferred) or ferric iron. While not intending to be limited by theory, it is believed that the acceptable taste of these iron complexes is due to the relatively large sizes of the sugar moiety and carboxylate counterion, which mask the usual "well-water" and/or brackish flavor of some iron supplements. This same mechanism is believed to be responsible for the low off-flavor noted when ferrous gluconate/ascorbate is used.

The overall synthesis of the preferred iron-sugar-carboxylate complexes used in the practice of this invention involves:

(a) forming a calcium-sugar moiety in aqueous media, for example, by reacting calcium hydroxide with a sugar;

(b) reacting an iron source, such as ferrous ammonium sulfate, with the calcium-sugar moiety in aqueous media to provide an iron-sugar moiety; and (c) neutralizing the reaction system with a carboxylic acid, for example, malic acid, to provide the desired iron-sugar complex.

The preferred iron II-sucrate-malate complex prepared in this manner is essentially equivalent to ferrous sulfate in iron bioavailability (measured as % change in hematocrit of test animals over the range of 0–9 ppm Fe), and, most importantly, is organoleptically acceptable in beverages, especially citrus beverages.

The "sugars" which can be employed in the preparation of iron compounds preferred for use in the practice of this invention include any of the ingestible saccharidic materials, and mixtures thereof, well-known in the culinary arts. For example, glucose, sucrose and fructose can conveniently be employed, with sucrose and fructose being the more preferred. However, other saccharidic materials can be used, for example mannose, galactose, lactose, maltose, and the like.

The "carboxylate counterion" used in the preparation of the preferred iron-sugar complexes herein can be any ingestible carboxylate species. However, some judgment must be made with regard to flavor contribution. For example, citrate, malate and ascorbate yield ingestible complexes whose flavors are judged to be quite acceptable, particularly in fruit juice beverages. Tartaric acid is acceptable, particularly in grape juice beverages, as is lactic acid. For essentially all purposes, the malate, citrate and ascorbate moieties suffice, although others can be selected, according to the desires of the formulator.

In a less preferred mode, the counterion for the iron-sugar complex can be noncarboxylate moieties such as phosphate, chloride, sulfate, or the like. However, such counterions can undesirably interact with calcium ions, especially in beverages. In high concentrations, these counterions may contribute an undesirable flavor note. Accordingly, the carboxylate counterions noted above are preferred herein.

The preparation of the preferred calcium source used herein, "calcium citrate-malate", is described in U.S. Pat. Nos. 4,786,510 and U.S. Pat. No. 4,786,518 issued to Nakel et al (1988) and U.S. Pat. No. 4,722,847 issued to Heckert (1988).

As noted above, iron bioavailability is normally somewhat impaired by the conjoint administration of calcium, but this impairment is overcome by use of the organic acids (citric and malic) and vitamin C in the vitamin and mineral supplemented beverages of this invention.

FLAVOR COMPONENT

The flavor component of the beverages and beverage concentrates of the present invention contains flavors selected from fruit flavors, botanical flavors and mixtures thereof. As used herein, the term "fruit flavor"

refers to those flavors derived from the edible reproductive part of a seed plant, especially one having a sweet pulp associated with the seed. Also included within the term "fruit flavor" are synthetically prepared flavors made to simulate fruit flavors derived from natural sources. Particularly preferred fruit flavors are the citrus flavors including orange, lemon, lime and grapefruit flavors. Besides citrus flavors, a variety of other fruit flavors can be used such as apple, grape, cherry, pineapple, mango and papaya flavors and the like. These fruit flavors can be derived from natural sources such as fruit juices and flavor oils, or can be synthetically prepared.

As used herein, the term "botanical flavor" refers to flavors derived from parts of a plant other than the fruit; i.e. derived from nuts, bark, roots and leaves. Also included within the term "botanical flavor" are synthetically prepared flavors made to simulate botanical flavors derived from natural sources. Examples of such flavors include kola, tea, and the like. Botanical flavors can be derived from natural sources such as essential oils and extracts, or can be synthetically prepared.

The flavor component can comprise a blend of various flavors, e.g. lemon and lime flavors, kola flavors and citrus flavors to form cola flavors, etc. If desired, fruit juices such as orange, lemon, lime, apple, grape and like juices can be used in the flavor component. The flavors in the flavor component are sometimes formed into emulsion droplets which are then dispersed in the beverage concentrate. Because these droplets usually have a specific gravity less than that of water and wOuld therefore form a separate phase, weighting agents (which can also act as clouding agents) are typically used to keep the emulsion droplets dispersed in the beverage. Examples of such weighting agents are brominated vegetable oils (BVO) and rosin esters, in particular the ester gums. See L.F. Green, *Developments in Soft Drinks Technology*, Vol. 1, (Applied Science Publishers Ltd. 1978), pp. 87-93, for a further description of the use of weighting and clouding agents in liquid beverages. Besides weighting agents, emulsifiers and emulsion stabilizers can be used to stabilize the emulsion droplets. Examples of such emulsifiers and emulsion stabilizers include the gums, pectins, celluloses, polysorbates, sorbitan esters and propylene glycol alginates. See L.F. Green, supra at p. 92.

The particular amount of the flavor component effective for imparting flavor characteristics to the beverages and beverage concentrates of the present invention ("flavor enhancing") can depend upon the flavor(s) selected, the flavor impression desired, and the form of the flavor component. The flavor component can comprise at least 0.05% by weight of the beverage composition, and typically from 0.1% to 2% by weight for carbonated beverages. When fruit juices are used as the flavor, the flavor component can comprise, on a single-strength basis, up to 25% fruit juice by weight of the beverage, preferably from 5% to 15% fruit juice by weight for carbonated beverages.

Carbonation Component

Carbon dioxide can be introduced into the water which is mixed with the beverage syrup or into the drinkable beverage after dilution to achieve carbonation. The carbonated beverage can be placed into a container such as a bottle or can and then sealed. Any conventional carbonation methodology can be used to make the carbonated beverages of this invention.

The amount of carbon dioxide introduced into the beverage will depend upon the particular flavor system used and the amount of carbonation desired. Usually, carbonated beverages of the present invention contain from 1.0 to 4.5 volumes of carbon dioxide. The preferred carbonated beverages contain from 2 to about 3.5 volumes of carbon dioxide.

Fruit Juice Components

The present invention is particularly suited for the preparation of beverages and beverage concentrates, including citrus juices. The beverages can contain from 3% to 100% juice or from about 0.05% to about 10% of an artificial or natural flavor, particularly orange juice. The concentrated orange juice, orange juice aroma and flavor volatiles, pulp and peel oils used in the method of the present invention can be obtained from standard orange juice. See Nagy et al, *Citrus Science and Technology*, Volume 2, (AVI Publishing Co. 1977), pp 177-252 for standard processing of oranges, grapefruit and tangerines. (See also Nelson et al, *Fruit and Vegetable Juice Processing Technology* (3rd Ed., AVI Publishing 1980),pp. 180-505 for standard processing of noncitrus juices such as apple, grape, pineapple, etc. to provide sources of juice and juice materials for vitamin mineral-supplemented noncitrus juice products).

Juices from different sources are frequently blended to adjust the sugar to acid ratio of the juice. Different varieties of oranges can be blended or different fruit juices can be blended to get the desired flavor and sugar to acid ratio. A sugar to acid ratio of from about 8:1 to about 20:1 is considered acceptable for fruit juices. However, preferred sugar to acid ratios are typically from about 11:1 to about 15:1, especially for citrus juices

Sweetener Component

Sweeteners include the sugars normally Present in fruit juice products, for example glucose, sucrose, and fructose. Sugars also include high fructose corn syrup, invert syrup, sugar alcohols, including sorbitol, refiners syrup, and mixtures thereof.

In addition to sugar, extended fruit juice beverages of the present invention can contain other sweeteners. Other suitable sweeteners include saccharin, cyclamates, acetosulfam, L-aspartyl-L-phenylalanine lower alkyl ester sweeteners (e.g. aspartame), L-aspartyl-D-alanine amides disclosed in U.S. Pat. No. 4,411,925 to Brennan et al., issued Oct. 23, 1983, L-aspartyl-D-serine amides disclosed in U.S. Pat. No. 4,399,163 at Brennan et al., issued Aug. 16, 1983, L-aspartyl-L-1-hydroxymethylalkaneamide sweeteners disclosed in U.S. Pat. No. 4,338,346 to Brand, issued Dec. 21, 1982, L-aspartyl-1-hydroxyethylakaneamide sweeteners disclosed in U.S. Pat. No. 4,423,029 to Rizzi, issued Dec. 27, 1983, L-aspartyl-D-phenylglycine ester and amide sweeteners disclosed in European Patent Application No. 168,112 to J.M. Janusz, published Jan. 15, 1986, and the like. A particularly preferred sweetener for use in such extended juice products is aspartame.

For single-strength fruit Juice beverages, the sugar content can range from about 2° to about 16° Brix. Typically, the sugar content of such beverages depends upon the amount of fruit juice contained herein. For full-strength beverages containing at least about 95% fruit juice, the sugar content is typically from about 5° to about 14° Brix. For extended juice beverages which comprise from about 50% to about 90% fruit juice, the sugar content is typically from about 5° to about 13°

Brix (no other sweetener) or from about 2° to about 8° Brix (other sweetener containing).

For fruit juice concentrates according to the present invention, the sugar content can range from about 6° to about 75° Brix. Typically, the sugar content of these juice concentrates is from about 20° to about 50° Brix. For orange juice concentrates, the sugar content is preferably from about 35° to about 50° Brix.

The amount of the sweetener effective in the beverages of the invention depends upon the particular sweetener used and the sweetness intensity desired. For noncaloric sweeteners, this amount varies depending upon the sweetness intensity of the particular sweetener. For sugar, this amount can be from 1% to 14% (typically from 6% to 14%) by weight for carbonated beverages. Preferred beverages contain from 9% to 13% by weight sugar. In determining the amount of sugar for beverages of the present invention, any sugar or other sweetener present in the flavor component, such as in fruit juice, is also included. Low-calorie sweetener combinations containing a noncaloric sweetener such as aspartame and a sugar such as high fructose corn syrup can also be used in beverages. For beverage syrups, the amount of sugar in a beverage syrup is from about 10% to about 60%, and preferably from about 40% to about 60%.

Method for Preparing Beverages and Beverage Concentrates Supplemented with Vitamin and Iron/Calcium The preferred overall method for preparing the liquid compositions herein involves preparing premix solutions of the iron and calcium complexes (see above) and mixing the premixes into the liquid compositions. The sugar or sugar alcohol is added in the desired amount, either as a solid or as a concentrated solution (e.g., 70% aqueous sorbitol, high fructose corn syrup, sucrose, corn syrup or refiners syrup) This method can be used to prepare iron and calcium supplemented beverages and concentrates, especially those based on citrus juices such as orange and grapefruit juice, noncitrus juices such as apple juice, as well as mixtures of juices which can be carbonated. The most preferred beverages are flavored carbonated beverages. In addition, this method will generally be used to make fruit juice beverages (including diluted 10–60% diluted "nectars") and juice concentrates. Orange juice beverages are also highly preferred fruit juice products according to the present invention.

Since beverage compositions comprising the vitamins, iron and the calcium supplements are more complicated to prepare than compositions containing only sugar and iron, preparation of the former compositions is described in detail.

In general, an acid component comprising citric acid and malic acid is typically dissolved in the appropriate quantity of water. (If desired, fruit juice or concentrated fruit juice such as lemon juice can be used to supply a portion of the acids.) Generally, this acid component comprises from 0 to about 90% by weight citric acid and from about 10% to 100% by weight malic acid. For orange juice, this acid component typically comprises from about 20% to about 90% by weight citric acid and from about 10% to about 80% by weight malic acid. Preferably, this acid component comprises from about 5% to about 60% by weight citric acid and from about 40% to about 95% by weight malic acid. (For noncitrus juices such as apple juice, this acid component typically comprises from about 5% to about 80% by weight citric acid and from about 20% to about 95% by weight malic acid, and preferably comprises from about 20% to about 50% by weight citric acid and from about 50 to about 80% by weight malic acid.) As a rule, the ratio of these acids is selected to provide optimum flavor character in the juice.

Once the solution containing the dissolved acids is formed, a source of calcium is then added. Calcium carbonate ($CaCO_3$) is a preferred calcium source. This calcium source leads to the greatest and most rapid initial solubilization of calcium and causes the least amount of off-flavor generation. Calcium hydroxide $[Ca(OH)_2]$ and calcium oxide (CaO) are also acceptable calcium sources, but can cause more off-flavor generation than calcium carbonate. The weight ratio of total acids to calcium added in the solution is typically from about 0.5 to about 12. Preferably, this weight ratio is from about 1 to about 6.

Addition of calcium carbonate, calcium oxide, or calcium hydroxide to the aqueous solution of acids provides a premix containing soluble and solubilizable calcium. This is due to the fact that highly soluble calcium citrate and malate species such as Ca(Hcitrate), $Ca(H_2citrate)_2$, and Ca(Hmalate) are formed in the solution due to the reaction between the calcium source and the acids. Without added stabilizers, the highly soluble calcium citrate species are stable in the premix solution for periods up to only about a few hours. After this short period of time, the highly soluble citrate species tend to disproportionate to the corresponding acid and the more thermodynamically stable, insoluble calcium citrate salts, such as $Ca_3(citrate)_2$.

To improve the stability of the more soluble calcium malate and especially citrate species in the premix solution, it is preferred in the method of the present invention to include a premix stabilizer. Materials which can complex with calcium and/or act as crystallization inhibitors are useful as premix stabilizers. These materials include sugars, such as sucrose, glucose, fructose, high fructose corn syrup, invert sugar, sugar alcohols, such as sorbitol, and polysaccharides such as pectin, algins, hydrolyzed starches, xanthan gum, and other edible gums. Concentrated juices which naturally contain both sugars and polysaccharides are particularly suitable premix stabilizers. Preferred premix stabilizers are sucrose and high fructose corn syrup (especially for extended juice products) and concentrated orange Juice having a sugar content of from about 35° to about 80° Brix whose source is described hereafter.

The premix stabilizer can be added immediately after the calcium source is added to the aqueous solution containing the acids. (When calcium carbonate is the calcium source, carbon dioxide evolution is preferably allowed to substantially cease before the premix stabilizer is added.) However, if desired, the premix stabilizer (especially in the case of sugars and concentrated Juice) can be added to the aqueous solution of the acids prior to addition of the calcium source. The amount of premix stabilizer included in the premix solution typically depends upon the stabilizer used. When sugars are used as the premix stabilizer, they are typically added in an amount sufficient to provide a sugar content of from about 2° to about 40° Brix. When polysaccharides are used, the amount can vary widely, but is typically from about 0.01% to about 0.5% on a weight/volume basis. When concentrated juice is used as the premix stabilizer, it is typically included in an amount sufficient to provide a sugar content of from about 2° to about 40° Brix (preferably from about 2° to about 24° Brix).

The premix solution of solubilized and solubilizable calcium is typically prepared in a batch-type fashion, as in the description above, at room temperature. However, this premix solution can also be prepared in a continuous fashion. In this continuous method, the ingredients (water, acids, calcium source and optional premix stabilizer) are constantly metered together to form the premix solution. The level at which the ingredients are metered is adjusted, as necessary, to insure appropriate solubilization of the calcium in the premix solution and to provide the appropriate acidity.

Separately, a premix solution of the iron-sugar complex is prepared. In general, this solution is somewhat simpler to prepare than the calcium-citrate-malate solution, above, since precipitation is not a major problem. Thus, a calcium-sugar reaction product is treated with an iron (preferably iron II) source, and the reaction product is neutralized with a carboxylic acid, in the manner described hereinabove. When ferrous gluconate/ascorbate is used it can be added to the calcium premix at this stage or at any other part of the process prior to the addition of vitamin C.

The premix solution of solubilized calcium is typically prepared in a batch-type fashion, as in the description above, at room temperature. However, this premix can also be prepared in a continuous fashion. In this continuous method, the ingredients (water, acids, calcium source, and optional premix stabilizer) are constantly metered together to form the premix solution. The level at which the ingredients are metered is adjusted, as necessary, to insure appropriate solubilization of the calcium in the premix solution and to provide the appropriate acidity.

When the iron-sugar complex or ferrous gluconate/ascorbate is added to this solution, it too is metered in.

To prepare a fruit flavored beverage, or flavored beverage, the premix is added to a concentrated beverage syrup or concentrate. The beverage concentrate syrup contains sugars.

The $\beta$-carotene and riboflavin can be added to the concentrated syrup either before, but, preferably, after the addition of the calcium premix. Flavors and flavor concentrates are added to the concentrated syrups. The syrup can be prepared by adding sugar to water which has preferably been degassed. A preservative, e.g. sodium benzoate, or butylated hydroxyanisole can be added. The riboflavin and $\beta$-carotene along with other vitamin are added to the syrup.

An alternative method of adding the calcium is as a dry mixture of calcium carbonate, citric acid and malic acid. This is added to the sugar/water solution in small amounts to avoid foaming.

When ferrous gluconate is used, it can be mixed with a small amount of vitamin C to stabilize the iron as ferrous iron. A ratio of about 2:1 vitamin C to active iron component in the ferrous gluconate is used in the solution. (Most ferrous gluconate is about 11% iron.) This solution contains ferrous gluconate/ascorbate which is a preferred iron source.

Flavors and colors can be added to the beverages at this point. Usually from about 0.05% to about 1% of flavorant is added. Artificial colors, natural colors, can also be added to produce the desired color and flavor of the beverage. Caffeine can also be added to the beverage or to the syrup.

After the syrup is made, the syrup tank is blanketed with carbon dioxide or nitrogen. Then the vitamin C is added. The syrup can be stored for later dilution to prepare single strength beverages or can be used immediately. In order to preserve the vitamin C, it is preferred that the syrup and the final beverage be blanketed with nitrogen or carbon dioxide both during the preparation and in the final package.

To make the final single strength beverage, the syrup is blended with water, preferably degassed water, at about 3 to 4 parts of water for 1 part syrup. The product is then ready to be packed as a degassed single strength "still" beverage or can first be carbonated, then packed as a single strength carbonated beverage. Degassed water is preferred since oxygen dissolved in the water will degrade the vitamin C.

To make a 100% juice product, the premix solution containing the solubilized calcium and the premix containing the solubilized iron are combined in a mix tank with chilled (e.g., below about 4.4° C.) concentrated fruit or citrus juice having a sugar content of from about 35° to about 80° Brix (preferably from about 60° to about 70° Brix), aroma and flavor volatiles, plus other juice materials such as pulp and peel oils, and the $\beta$-carotene, vitamin C and riboflavin are added to provide iron, calcium and vitamin supplemented juice products. The particular proportions of premix solution, concentrated juice, aroma and flavor volatiles, pulp and peel oils and vitamins used will depend upon a number of different factors, including the type of juice product involved (single-strength juice beverage or juice concentrate). For example, vitamin iron- and calcium-supplemented 42° Brix orange juice concentrates can be prepared by combining 65 parts concentrated orange juice (65° Brix), 5 parts pulp, 15 parts of an aroma/flavor concentrate, 0.4 parts peel oil with the 15 parts Fe/Ca premix. The vitamins are then added to this concentrate. Similar single-strength juice beverages can be prepared by appropriate variation of the amounts of concentrated juice, pulp, aroma/flavor concentrate, flavor oil and premix solutions, as well as the inclusion of water.

Juice compositions and other beverages are preferably formulated at a pH below about 4.3, generally about 3 7–4.0, for reasons of microbial stability.

After the vitamin, iron and calcium supplemented juice product is obtained, it is then filled into cans, cartons, bottles or other appropriate packaging. In the case of citrus juice concentrates, these products are typically frozen after being filled into cans.

pH and Other Beverage Ingredients

The pH of the beverages and beverage concentrates of the present invention is dependent upon the particular composition of the acid component, the total amount of acids used and the sourness impression desired. Typically, the pH can range from 2.5 to 5.0. Preferred carbonated beverages have a pH of from 3.0 to 4.5.

Other minor beverage ingredients are frequently included in beverages and concentrates. Such ingredients include preservatives such as benzoic acid and salts thereof, sulfur dioxide, butylated hydroxyanisole, etc. Also, typically included are colors derived either from natural sources or synthetically prepared. See L.F. Green, Developments in Soft Drinks Technology, Vol. 1 (Applied Science Publishers Ltd. 1978), pp. 185–186 for preservatives and colors used in beverages. Caffeine may also be included.

Packaging

The beverages, beverage concentrates and nectars are degassed to remove oxygen from the solution. This degassing may occur by bubbling carbon dioxide or nitrogen through the solution or by sterilizing the solution under vacuum or by simply heating the solution under vacuum to remove dissolved oxygen. The degassing should occur before the addition of the carbonated water, if a beverage is to be carbonated.

In order to maintain the stability of the iron salts, and to keep the vitamin C from oxidizing, the beverage should be packaged under nitrogen or carbon dioxide or other inert common non-oxidizing gaseous mixtures. This is within the skill of one in the art to pack the beverages in this manner. Preferably, the beverages are bottled in opaque bottles to protect them from sunlight or a oxygen scavenger or other free radical scavenger is added to prevent oxidation caused by ultraviolet light.

The following example illustrates beverage compositions of the type provided by the practice of this invention, but is not intended to be limiting thereof.

EXAMPLE I

A carbonated soft drink is prepared as follows:

| Ingredient | Amount (grams) |
| --- | --- |
| Granular Sucrose | 13.39 |
| Citric Acid | 0.17 |
| Sodium Benzoate | 0.05 |
| Starch | 0.02 |
| Flavor Oil | 0.008 |
| Ester Gum | 0.0065 |
| Colors | 0.006 |
| Butylated Hydroxyanisole (BHA) | 0.00004 |
| Riboflavin | 0.0003 |
| Ascorbic Acid | 0.007 |
| β-Carotene* | 0.06 |
| Ferrous Gluconate (11.6%) | 0.008 |
| Calcium Chloride | 0.11 |
| Water | 36.9 |
| Carbonated Water | 49.02 |

*1% CWS powder from Hoffman La Roche, Nutley, N.J.

Water (10 grams) is used to dissolved the sodium benzoate, riboflavin, β-carotene and sugar. To this solution is added the calcium chloride. Separately a solution of ferrous gluconate and part of the vitamin C (ascorbic acid, 0.008 grams) is prepared in a portion of the remaining water. This makes a ferrous gluconate/ascorbate mixture which is then added to the concentrate. A flavor concentrate containing flavor oils, gums, colors, starch and BHA are then added to this concentrate.

Finally the remaining vitamin C is added to the syrup after the syrup is blanketed with nitrogen. This final syrup is diluted with the carbonated water.

This carbonated drink (180 ml) has a recommended daily allowance of 21% vitamin C, 11% to 12% calcium, 10% iron, 32% riboflavin, and 18% vitamin A equivalent.

| Example II | |
| --- | --- |
| Ingredient | Amount (grams) |
| Granular Sucrose | 12.63 |
| Sodium Benzoate | 0.05 |
| Starch | 0.02 |
| Flavor Oil | 0.008 |
| Ester Gum | 0.0065 |
| Colors | 0.006 |
| Butylated Hydroxyanisole (BHA) | 0.00004 |

| -continued | |
| --- | --- |
| Example II | |
| Ingredient | Amount (grams) |
| Riboflavin | 0.0003 |
| Ascorbic Acid | 0.007 |
| β-Carotene* | 0.06 |
| Ferrous Gluconate (11.6%) | 0.008 |
| Citric Acid | 0.025 |
| Malic Acid | 0.14 |
| Calcium Carbonate | 0.16 |
| Water | 10.9 |
| Carbonated Water | 75.8 |

*1% CWS powder from Hoffman La Roche, Nutley, N.J.

This beverage is prepared and packaged as in Example 1, except that the calcium carbonate, citric and malic acids are premixed dry and then added in small increments to prevent excessive foaming. The amount of riboflavin and β-carotene remain at nearly 100% of their initial levels after 2 months of storage. The ascorbic acid shows acceptable stability.

Beverages prepared according to Examples I & II along with other test samples are labelled either with radioactive Calcium [$^{47}$Ca] or iron [$^{59}$Fe]. These samples are then fed to test rats by gavaging each animal with about 5 ml of the sample. The radioactivity is measured using a whole body gamma counter at zero (0) time and after three days for the calcium labelled material and after six days for the iron labelled material. The percent of radioactive calcium or iron retained in the whole animal after this time period is an indication of the bioavailability of the mineral. The bioavailability of the calcium is determined separately from the bioavailability of the iron.

Bioavailability of Calcium as Assayed by Whole Body Isotope Retention in Rats Each animal received either 3 mg Ca (Example II) or 2 mg Ca (Example I). The Ca was dosed with $^{47}$Ca (1 $\mu$Ci $^{47}$CaCl$_2$).

EXAMPLE I when CaCl$_2$ was used as $^{47}$Ca source

| Treatments | [$^{47}$Ca] Retention (% SEM)* |
| --- | --- |
| 1. Carbonated beverage (12% RDA Ca) (Example I) | 82.7 ± 2.9 |
| 2. CaCl$_2$ in H$_2$O (12% RDA Ca) | 41.2 ± 3.2 |
| 3. Diluted Milk (12% RDA Ca) | 39.2 ± 3.9 |

*SEM - standard experimental mean

The carbonated beverage of Example I has twice the calcium retention of diluted milk or calcium chloride in water.

Example II when Calcium-Citrate-Malate is the $^{47}$Ca source

| Treatments | [$^{47}$Ca] Retention (% ± SEM) |
| --- | --- |
| 1. Carbonated beverage (Example II) | 75.4 ± 4.0 |
| 2. CaCO$_3$ + citrate + malate | 35.0 ± 2.4 |
| 3. Milk - diluted | 32.6 ± 2.0 |

The carbonated beverage of Example II has twice the calcium retention of diluted milk and calcium-citrate-malate in water.

Bioavailability of Iron as Assayed by Whole Body Isotope Retention Rats

| Treatments | [$^{59}$Fe] Retention (% SEM) |
|---|---|
| 1. Carbonated beverage (Example II) | 42.1 ± 2.6 |
| 2. Fe-Gluconate/ascorbate in H$_2$O | 38.6 ± 4.6 |
| 3. Fe-Gluconate/ascorbate + CCM* in H$_2$O | 33.6 ± 2.0 |
| 4. Fe-Gluconate + CCM* in H$_2$O | 28.3 ± 1.7 |
| 5. FeSO$_4$ in H$_2$O | 42.9 ± 2.9 |
| 6. FeSO$_4$ in H$_2$O + CCM* | 27.9 ± 3.5 |

*CCM is a mixture of calcium, citrate and malate.

This test shows that even though calcium is present, the iron remains as bioavailable in the carbonated beverage as the ferrous sulfate in water.

EXAMPLE III

The following illustrates the preparation of a preferred calcium and iron compounds for use in the practice of this invention, but is not intended to be limiting thereof.

Preparation of Iron II Sucrate-Malate

Sucrose (85.5 g) is dissolved in water (299.8 g), making sure that dissolution is complete. Calcium hydroxide (18.5 g) is then added, and the mixture is stirred for 5 minutes. If any clouding is observed, the resulting solution is filtered through a glass filter.

To the resulting calcium-sucrate solution is added ferrous ammonium sulfate (24.5 g), and the solution is covered air-tight (e.g., SARAN WRAP). The green color indicates the iron is in the desired II oxidation state.

To the above solution is added malic acid (33.5 g) in 3 batches, to pH 3-4. The precipitate is filtered through standard filter paper, but the filter cake comprising calcium sulfate is not rinsed. The resulting solution comprises the iron sucrate-malate used in the practice of this invention. The solution can be used per se, or can be freeze-dried to provide the iron sucrate-malate in powder form.

In an alternate mode, KOH can be substituted for Ca(OH)$_2$ in the first step, but sulfate ion will be left in the final product.

Variations in the method for preparing iron-sugar complexes, as well as alternate sugars and counterions, are given in the following examples.

Preparation of Calcium-Citrate-Malate

A calcium-citrate-malate solution is prepared by dissolving 2 parts sucrose and then 0.1 part citric and 0.28 part malic acids in 28.19 parts water. Calcium hydroxide (0.22 part) is added and the mixture is agitated. This solution can be used directly to prepare beverages, or can be freeze-dried to use in solid form.

EXAMPLE IV Beverage Compositions

The following beverage compositions (a-i) are fortified with the iron (II) sucrate-malate and calcium citrate-malate as prepared below to provide 10% RDA of iron and 100% RDA calcium per 180 ml serving. β-carotene encapsulated in dextrin (18%), riboflavin (32%) and ascorbic acid (25%) are added to each composition to enhance iron/calcium bioavailability and to provide vitamin supplements.

(a) "sparkling" orange juice comprising 55% orange juice and 45% carbonated water;
(b) pear-grapefruit nectar comprising 25% pear juice, 20% grapefruit Juice, the balance comprising 10% sucrose-water;
(c) kiwi-grapefruit drink comprising 20% kiwi fruit juice, 15% grapefruit juice, the balance comprising water;
(d) mixed fruit "cocktail" comprising 10% each of the juices of passion fruit, mango, guava, pineapple, papaya, banana, apricot, mandarin orange, pear and lime juices;
(e) yogurt/fruit beverage comprising 20% milk products, 1% pectin, 20% pineapple juice, 10% shredded pineapple fruit pulp, 16% corn syrup, the balance comprising water;
(f) cola beverage comprising 0.35% cola flavor emulsion, 11% sugar, 0.1% phosphoric acid, 0.1% citric and malic acids, caramel coloring, the balance comprising carbonated water;
(g) full-strength orange juice;
(h) full-strength apple juice;
(i) full-strength flavored cow's milk.

What is claimed is:

1. A stable nutritional vitamin and mineral supplemented beverage or beverage concentrate, comprising a mixture of:
   (i) a nutritionally supplemental amount of encapsulated β-carotene, vitamin C and riboflavin;
   (ii) a nutritionally supplemental amount of an iron-sugar complex or iron gluconate/ascorbate;
   (iii) a nutritionally supplemental amount of a calcium source;
   (iv) at least about 0.1% of weight of flavor, or at least 3% by weight of fruit juice; and
   (v) water.

2. A beverage according to claim 1 wherein said calcium source is selected from the group consisting of calcium chloride, calcium carbonate, calcium-citrate-malate and mixtures thereof.

3. A beverage according to claim 2 wherein the amount of β-carotene, vitamin C and riboflavin is from about 10% to about 300% RDA.

4. A beverage according to claim 3 wherein said water is degassed.

5. A beverage concentrate according to claim 4 which comprises at least about 40% sugar.

6. A beverage concentrate according to claim 5 which contains caffeine.

7. A beverage concentrate according to claim 4 which additionally contains an artificial sweetener.

8. A beverage according to claim 4 wherein the iron source is selected from the group of ferrous gluconate/ascorbate or an iron-sugar complex wherein the counterion is selected from malate, citrate, tartrate, ascorbate, or mixtures thereof.

9. A beverage according to claim 8 wherein the iron-sugar complex is iron sucrate-malate, iron fructate-malate, iron gluconate/ascorbate or mixtures thereof.

10. A beverage according to claim 4 which is carbonated.

11. A beverage according to claim 4 wherein the β-carotene is encapsulated in dextrin, gum acacia, or mixtures thereof.

12. A beverage according to claim 11 which is carbonated.

13. A beverage according to claim 12 which comprises from about 5% to about 15% sweetener.

14. A beverage according to claim 13 wherein the sweetener is selected from the group consisting of sucrose, fructose, glucose, high fructose corn syrup, corn syrup and mixtures thereof.

15. A beverage according to claim 12 which contains a nutritionally supplemental amount of calcium-citrate-malate.

16. A beverage according to claim 12 which comprises from about 0.05% to about 1% of a natural or botanical flavor or mixtures thereof.

17. A beverage according to claim 11 which comprises an artificial sweetener.

18. A composition according to claim 11 wherein the fruit juice is selected from grape, pear, passion fruit, cherry, pineapple, banana or banana puree, apricot, orange, lemon, grapefruit, apple, cranberry, tomato, mango, papaya juices and mixtures thereof.

19. A beverage according to claim 11 wherein the mixture further comprises a sugar alcohol selected from sorbitol, mannitol and mixtures thereof.

20. A beverage according to claim 11 which comprises at least 10% sucrose.

* * * * *

UNITED STATES PATENT AND TRADEMARK OFFICE
CERTIFICATE OF CORRECTION

PATENT NO. : 4,992,282

DATED : 2/12/91

INVENTOR(S) : H. Mehansho et al.

It is certified that error appears in the above-identified patent and that said Letters Patent is hereby corrected as shown below:

Column 18, line 36, after "water" insert -- and (vi) color. --.

Signed and Sealed this

Twenty-fifth Day of August, 1992

Attest:

DOUGLAS B. COMER

*Attesting Officer*    Acting Commissioner of Patents and Trademarks